United States Patent [19]

Ohta et al.

[11] Patent Number: 5,656,637
[45] Date of Patent: Aug. 12, 1997

[54] THIAZOLE DERIVATIVES

[75] Inventors: Mitsuaki Ohta, Ibaraki; Isao Yanagisawa, Tokyo; Keiji Miyata, Ibaraki, all of Japan

[73] Assignee: Yamanouchi Pharmaceutical Co., Ltd., Tokyo, Japan

[21] Appl. No.: 334,378

[22] Filed: Nov. 3, 1994

Related U.S. Application Data

[63] Continuation of Ser. No. 50,123, Apr. 23, 1994, Pat. No. 5,424,431.

[30] Foreign Application Priority Data

Oct. 24, 1990 [JP] Japan ........................ 2-286902

[51] Int. Cl.$^6$ .................... C07D 417/06; A61K 31/465
[52] U.S. Cl. .................... 514/301; 514/326; 514/342; 546/114; 546/209; 546/270.4; 548/190; 548/195; 548/196; 548/200
[58] Field of Search .................. 546/114, 209, 546/280; 514/301, 326, 342; 548/190, 195, 196, 200

[56] References Cited

FOREIGN PATENT DOCUMENTS 3406329  8/1985  Germany.

Primary Examiner—Robert Gerstl
Attorney, Agent, or Firm—Sughrue, Mion, Zinn, Macpeak & Seas

[57] ABSTRACT

A novel thiazole derivative represented by general formula (I), which has a selected agonistic activity for 5-HT$_3$ receptor, a pharmaceutical composition thereof, and a process for producing the same. In the said formula, $R^1$ represents hydrogen or lower alkoxy; $R^2$ and $R^3$ are such that $R^2$ represents hydrogen and $R^3$ represents a group, —Y—Het, wherein Y represents a single bond or lower alkylene and Het represents a nitrogenous heterocyclic group, or alternatively $R^2$ and $R^3$ are combined together to form a group, —(CH$_2$)$_m$—NR$^4$—(CH$_2$)$_n$—, wherein m and n are each 1 or 2 and $R^4$ represents lower alkyl; and X represents —NH—, —NHC(=O)NH—, —C(=O)NH— or —NHC(=O)—.

9 Claims, No Drawings

THIAZOLE DERIVATIVES

This is a continuation of application Ser. No. 08/050,123 filed Apr. 23, 1994, now U.S. Pat. No. 5,424,431.

TECHNICAL FIELD

The present invention relates to novel thiazole derivatives and pharmaceutically acceptable salts thereof having 5-HT$_3$ receptor agonist activity, pharmaceutical compositions thereof, and processes for producing the same.

BACKGROUND ART

While it is acknowledged that, roughly classified, there are 4 types of serotonin (5-HT) receptors, the neuronal serotonin (5-HT) receptors located in the primary afferent nerves of the enteric nervous system or of the central nervous system are considered, as of this day, to be 5-HT$_3$ receptors. Regarding such 5-HT$_3$ receptors, many compounds having 5-HT$_3$ receptor antagonist activity have so far been discovered. For example, the compounds described in British Patents 2,125,398, 2,166,726, 2,126,728 and 2,153,821 are known to have such activity. However, there has not been discovered a compound having selective 5-HT$_3$ receptor agonist activity.

DISCLOSURE OF INVENTION

The inventors of the present invention conducted extensive studies regarding 5-HT$_3$ receptors, created a variety of compounds and subjected them to a screening. As a result, they discovered that a novel thiazole derivative of the following general formula (I) possesses excellent selective 5-HT$_3$ receptor agonist activity and accomplished the present invention. The thiazole derivative of the general formula (I) exhibits its action by inducing release of acetylcholine from the efferent nerve endings. It is thought that any 5-HT$_3$ receptor agonist drug is useful particularly in disorders of the digestive system.

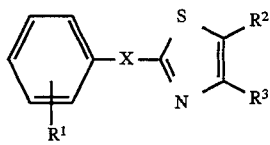

(wherein R$^1$ means or a lower alkoxy group, R$^2$ and R$^3$ are either such that R$^2$ means a hydrogen atom and R$^3$ means a group of the formula —Y—Het (where Y means a single bond or a lower alkylene group and Het means a nitrogen-containing heterocyclic group) or such that R$^2$ and R$^3$ combined together mean a group of the formula

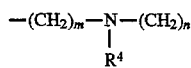

(where m and n each means 1 or 2 and R$^4$ means a lower alkyl group), and X means a group represented by one of the following formulas: —NH—,

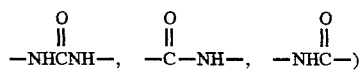

It is, therefore, an object of the present invention to provide a thiazole derivative of the above general formula (I) or a pharmaceutically acceptable salt thereof.

Another object of the present invention is to provide a pharmaceutical composition comprising aforementioned derivative or salt, and a pharmaceutically acceptable carrier.

It is still another object of the present invention to provide processes for producing the aforementioned derivative or salt.

The compound of the above general formula (I) is now described in further detail.

Throughout this specification, the term "lower" means, unless otherwise indicated, a straight or branched carbon chain containing 1 to 6 carbon atoms.

Thus, the "lower alkyl group" includes methyl, ethyl, propyl, isopropyl, butyl, isobutyl, sec-butyl, tert-butyl, pentyl, isopentyl, hexyl, isohexyl and so on. The group meant by "lower alkoxy group" includes methoxy, ethoxy, propoxy, isopropoxy, butoxy, isobutoxy, sec-butoxy, tert-butoxy, pentyloxy, isopentyloxy, hexyloxy, isohexyloxy and so on. Furthermore, "lower alkylene group" includes methylene, ethylene, methylmethylene

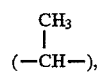

trimethylene, 1-methylethylene

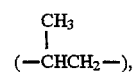

2-methylethylene,

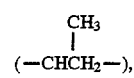

tetramethylene, 1-methyltrimethylene, 2-methyltrimethylene, 1-ethylethylene, 2-ethylethylene, pentamethylene, 1-methyltetramethylene, 2-methyltetramethylene, 3-methyltetramethylene, 4-methyltetramethylene, hexamethylene and so on.

Moreover, the nitrogen-containing heterocyclic group forming R$^3$ means a 5- to 6-membered heterocyclic group containing 1 nitrogen atom. Representative species of the heterocyclic group are pyrrolidinyl, pyrrolyl, piperidyl, pyridyl and so on.

The compound of the present invention contains double bonds and may contain asymmetric carbon atoms depending on substituent groups. Therefore, the compound of the present invention include various mixtures of isomers and individual isomers, such as geometrical isomers, tautomers and optical isomers.

The compound (I) of the present invention may form acid addition salts. Among specific such salts are addition salts with mineral acids such as hydrochloric acid, hydrobromic acid, hydroiodic acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, etc. and acidic amino acids such as aspartic acid, glutamic acid, etc.

Production Processes

The compound and salt of the present invention can be produced by application of a variety of synthetic processes utilizing the respective features of their skeletal structures or substituent groups. Some representative processes are now described below by way of example.

Process 1

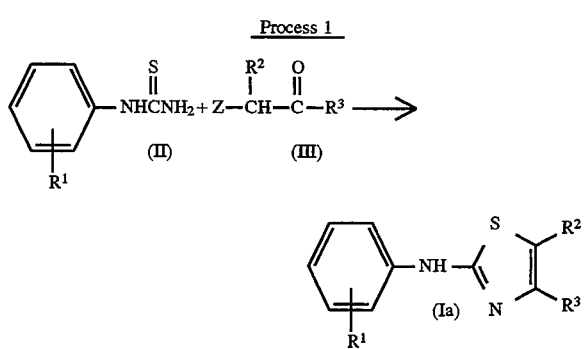

(wherein $R^1$, $R^2$ and $R^3$ have the meanings respectively defined hereinbefore and Z means a halogen atom such as Cl and Br)

This production process comprises reacting a thiourea derivative of the general formula (II) with an α-halogenoketone derivative of the general formula (III) to synthesize a thiazole derivative of the general formula (Ia). This reaction is, for example, conducted in a solvent such as alcohol, acetone, ether, tetrahydrofuran, digrime, dioxane, etc. at room temperature or under warming.

Production Process 2

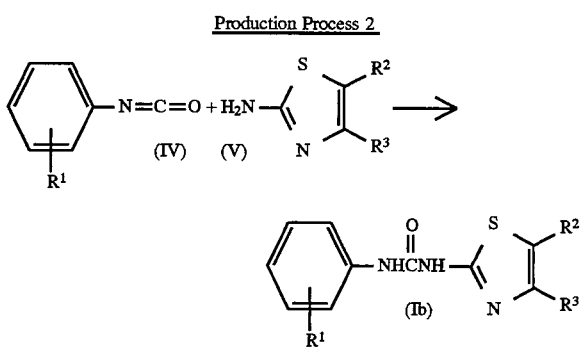

(wherein $R^1$, $R^2$ and $R^3$ have the meanings respectively defined hereinbefore)

This production process comprises reacting an isocyanate derivative of the general formula (IV) with an amine compound of the general formula (V) to synthesize an urea derivative of the general formula (Ib). This reaction is generally conducted in a solvent such as chloroform, dichloromethane, 1,2-dichloroethane, ether, tetrahydrofuran, acetone, etc., under cooling or at room temperature.

Production Process 3

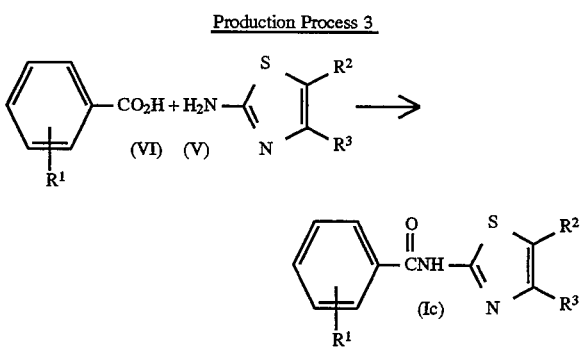

(wherein $R^1$, $R^2$ and $R^3$ have the meanings respectively defined hereinbefore)

This production process comprises reacting a carboxylic acid derivative of the general formula (VI) with an amine derivative of the general formula (V) to synthesize an amide derivative of the general formula (Ic). This reaction is generally conducted using an activating agent of a carboxylic acid, such as ethyl chlorocarbonate or, dicyclohexylcarbodiimide (DCC) and 1-hydroxybenzotriazole (HOBT), in a solvent such as methylene chloride, chloroform, 1,2-dichloroethane, dimethylformamide, etc. under cooling or at room temperature.

Production Process 4

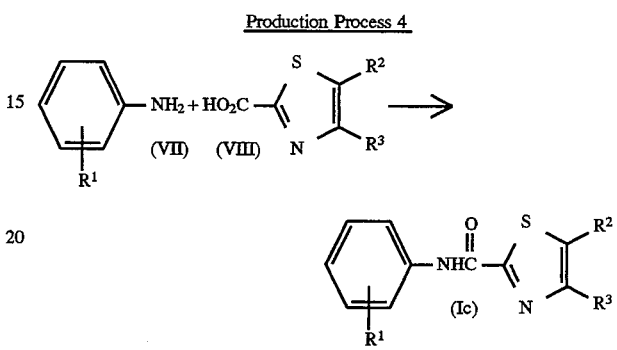

(wherein $R^1$, $R^2$ and $R^3$ have the meanings respectively defined hereinbefore)

This process comprises reacting an amine derivative of the general formula (VII) with a carboxylic acid derivative of the general formula (VIII) to synthesize an amide derivative of the general formula (Id).

This process is carried out in the same manner as Production Process 3.

INDUSTRIAL APPLICABILITY

By acting specifically on the neuronal 5-$HT_3$ receptors located in the enteric nervous system, the compounds of the present invention are useful for the treatment of disorders of the digestive system, namely senile constipation, atonic constipation, diabetic motor disorder of the digestive tract, postoperative motor disorder of the digestive tract, retention of gastric contents, dyspepsia, flatulence and so on.

Furthermore, since the compound of the present invention shows a behavior analogous to that of 5-HT toward the inhibitory presynaptic 5-$HT_3$ receptors located in the central nervous system, it is useful for the treatment of such symptoms as mental disorders (for example, schizophrenia and depression), anxiety and dysmnesia. In addition, it is foreseen that through activation of dopaminergic neurons in the central nervous system, it may find application in improving extrapyramidal symptoms (particularly parkinsonism).

The pharmacologic actions of the compound of the present invention were confirmed by the following methods (Bezold-Jarisch reflex in anesthetized rat).

Male Wistar rats, 9 weeks old, were anesthetized with urethane 1 g/kg i.p. and the blood pressure and the heart rate were determined under artificial ventilation. The transient decreases in heart rate and blood pressure that were induced by intravenous administration of the compound of the present invention were evaluated as indicators of 5-$HT_3$ receptor-mediated responses (Bezold-Jarisch reflex; Paintal. A. S., Physiol. Rev., 53, 159 (1973)) and compared with the responses to serotonin and 2-methylserotonin which is a selective 5-$HT_3$ agonist. In addition, it was confirmed by using 5-$HT_3$ receptor antagonists that the changes caused by administration of the compound of the present invention were 5-HT$_3$ receptor-mediated responses.

1) 5-HT$_3$ receptor stimulating action (Bezold-Jarisch reflex evoking action)

The compound and salt of the present invention, given intravenously (0.3–30 μg/kg), depressed the heart rate and blood pressure dose-dependently and these effects were more prominent than those of serotonin or 2-methylserotonin which is a selective 5-HT$_3$ agonist. The Bezold-Jarisch (BJ) reflex evoking action of the compound of the present invention in rats is shown in the following table.

The compound of Example 1 was about 5-fold as potent as serotonin in the above-mentioned Bezold-Jarisch reflex evoking activity.

| | BJ reflex evoking activity | |
|---|---|---|
| | ED$_{50}$ (μg/kg i.v.) | Emax (beats/min) (maximal bradycardiac response) |
| Compound of Example 1 | 3.01 | 205.8 |
| Serotonin | 15.6 | 257.9 |
| 2-Methylserotonin | 37.4 | 259.0 |

2) Effects of 5-HT$_3$ receptor antagonists on the action of the compound of the present invention The decreases in heart rate and blood pressure as induced by the compound of the present invention were competitively inhibited by administering a 5-HT$_3$ receptor antagonist, viz. GR38032F (30 μg/kg i.v.) or ICS 205–930 (0.1–1 μg/kg i.v.), 10 minutes before administration of the compound of the present invention.

The above results 1) and 2) indicate that the compound of the present invention is a potent and selective 5-HT$_3$ receptor agonist.

The compound of the present invention is sparingly toxic, with an acute toxicity value (the up and down method) of 50 to 100 mg/kg i.v. for male mice.

The pharmaceutical composition containing one or more species of the compound and salt of the present invention as the active ingredient is formulated with the conventional pharmaceutical carrier, excipient and/or other additives, into tablets, powders, fine granules, capsules, pills, solutions, injections, suppositories, ointments, plasters, etc., and administered orally (inclusive of sublingual administration) or parenterally.

The pharmaceutical carrier or excipient includes a variety of solid or liquid nontoxic substances for pharmaceutical use. Among them are lactose, magnesium stearate, starch, talc, gelatin, agar, pectin, gum arabic, olive oil, sesame oil, cacao butter, ethylene glycol and other substances which are commonly employed.

The clinical dosage of the compound of the present invention is appropriately determined according to the condition, body weight, age, sex, and other factors of the patient being treated, but generally the daily dosage for the adult human is 0.2 to 2 mg for intravenous injection or 1 to 10 mg for oral administration, to be administered in a single dose or in a few divided doses.

FORMULATION EXAMPLES

The following are typical pharmaceutical formulation examples for the compound of the present invention.

| (1) Tablets | |
|---|---|
| Compound of Example 1 (hereinafter referred to as compound A) | 0.2 mg |
| Lactose | 106.4 mg |
| Corn starch | 48.0 mg |
| Hydroxypropylcellulose | 4.8 mg |
| Magnesium stearate | 0.6 mg |
| | 160.0 mg/tablet |

First, 200 mg of compound A, 106.4 g of lactose and 48 g of corn starch are evenly blended and, after adding 48 ml of a 10% aqueous solution of hydroxypropylcellulose, the mixture is granulated using a granulating machine. Then, 0.6 g of magnesium stearate is added to the granules and the whole mixture is compression-molded to provide tablets each weighing 160 mg (1000 tablets).

| (2) Powders | |
|---|---|
| Compound A | 0.4 mg |
| Mannit | 770.0 mg |
| Corn starch | 199.6 mg |
| Polyvinylpyrrolidine | 30.0 mg |
| | 1000.0 mg |

First, 0.4 g of compound A, 770 g of mannit and 199.6 g of corn starch are evenly blended and, then, 300 ml of a 10% aqueous solution of polyvinylpyrrolidone is added. The mixture is then granulated using a granulation machine to provide powders (1 kg).

| (3) Capsules | |
|---|---|
| Compound A | 0.2 mg |
| Corn starch | 198.8 mg |
| Calcium stearate | 1.0 mg |
| | 200.0 mg |

First, 0.2 g of compound A, 198.8 g of corn starch and 1 g of calcium stearate are evenly blended and the mixture is filled in 200 mg portions into No. 3 capsule shells to provide capsules (1000 capsules).

| (4) Syrup | |
|---|---|
| Compound A | 0.2 mg |
| Sucrose | 8.0 mg |
| Water to make | 5 ml |

A syrup is prepared by dissolving 0.2 g of compound A and 8 g of sucrose in sufficient pure water to make 5 l.

(5) Injectable solution for intravenous administration

| Compound A | 0.3 mg |
|---|---|
| Sodium chloride | 9 mg |
| Distilled water for injection to make | 1.0 ml |

First, 300 mg of compound A and 9 g of sodium chloride are dissolved in sufficient distilled water for injection use to make 1000 ml. After filtration, this solution is filled in 1 ml portions into ampuls to provide injections. In the process, air in each ampul is replaced with nitrogen gas. The ampuls are then heat-sterilized by autoclaving (1000 ampuls).

EXAMPLES

The following examples are intended to describe the present invention in further detail.

Example 1

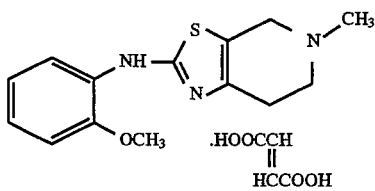

(1) To 50 ml of acetone were added 2.46 g of o-anisidine and 3.75 g of benzoyl isothiocyanate, and the mixture is stirred under reflux for 2 hours and, then, allowed to stand overnight in a refrigerator at 5° C. The resulting crystals were collected by filtration, washed with cold acetone and dried under reduced pressure. The crystals were added to 50 ml of 30% methylamine-methanol and the mixture was stirred at room temperature overnight. The reaction mixture was concentrated to dryness under reduced pressure, and the residue was washed with ethanol-ethyl acetate and dried under reduced pressure. The procedure provided 2.08 g of N-(o-methoxyphenyl)thiourea.

Physicochemical properties:

$^1$H Nuclear magnetic resonance spectrum (δ, DMSO-d$_6$): 3.84 (s, 3H), 6.80–7.24 (m, 3H), 7.76–7.88 (dd, 1H)

Mass spectrum (FAB): m/z 183 (M$^+$+1)

(2) To 2 ml of ethanol were added 0.6 g of 3-bromo-1-methylpiperidin-4-one hydrobromide and 0.37 g of the compound synthesized in (1) and the mixture was stirred at 80° C. for 30 minutes. The mixture was then concentrated to dryness under reduced pressure, and the residue was diluted with aqueous sodium hydrogencarbonate solution and extracted with ether. The extract was dried over anhydrous magnesium sulfate and concentrated to dryness under reduced pressure. The residue was treated with a suitable amount of fumaric acid in methanol-acetonitrile and the resulting crystals were collected by filtration to provide 0.25 g of 2-(o-methoxyanilino)-5-methyl-4,5,6,7-tetrahydrothiazolo[5,4-c]pyridine fumarate.

Physicochemical properties:

Melting point: 185°–190° C. (decomp.)

| Elemental analysis (for C$_{14}$H$_{17}$N$_3$OS.C$_4$H$_4$O$_4$.0.6H$_2$O): | | | |
|---|---|---|---|
| | C(%) | H(%) | N(%) |
| Calcd. | 53.76 | 5.56 | 10.45 |
| Found | 53.75 | 5.53 | 10.53 |

Mass spectrum (EI): m/z 275 (M$^+$, free compound)

Example 2

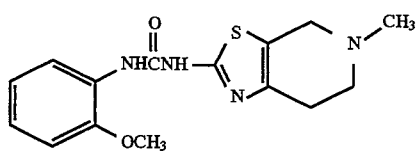

(1) To 11 ml of ethanol were added 0.86 g of thiourea and 3.08 g of 3-bromo-1-methylpiperidin-4-one hydrobromide, and the mixture was stirred under reflux for 1 hour. The reaction mixture was then concentrated to dryness under reduced pressure, and the residue was diluted with aqueous sodium carbonate solution and extracted with dichloromethane.

The organic layer was concentrated to dryness under reduced pressure and subjected to column chromatography (silica gel; chloroform-methanol) to provide 0.56 g of 2-amino-5-methyl-4,5,6,7-tetrahydrothiazolo[5,4-c]pyridine as powders.

Physicochemical properties:

$^1$H Nuclear magnetic resonance spectrum (δ, CDCl$_3$): 2.50 (s, 3H), 2.60–2.80 (m, 4H), 3.40–3.50 (m, 2H)

Mass spectrum (EI): m/z 169 (M$^+$)

(2) To 5 ml of dichloromethane were added 0.17 g of the compound obtained in (1) and 0.15 g of (o-methoxyphenyl) isocyanate and the mixture was stirred at room temperature overnight. The reaction mixture was then concentrated to dryness under reduced pressure, subjected to column chromatography (silica gel; chloroform-methanol) and washed with ethyl acetate. This procedure provided 0.25 g of N-(o-methoxyphenyl)-N'-(5-methyl-4,5,6,7-tetrahydrothiazolo[5,4-c]pyridin-2-yl)urea melting at 201°–203° C.

Physicochemical properties:

| Elemental analysis (for C$_{15}$H$_{18}$N$_4$O$_2$S): | | | |
|---|---|---|---|
| | C(%) | H(%) | N(%) | S(%) |
| Calcd. | 56.58 | 5.70 | 17.60 | 10.07 |
| Found | 56.38 | 5.64 | 17.46 | 10.14 |

Mass spectrum (EI): m/z 318 (M$^+$)

Example 3

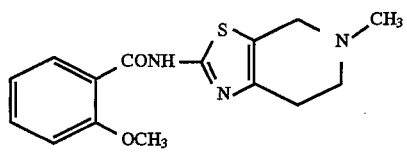

To a solution of 0.15 g of o-methoxybenzoic acid in 2 ml of DMF was added 0.16 g of HOBT followed by addition of 0.25 g of DCC. After 30 minutes, 0.17 g of the compound obtained in Example 2-(1) was added and the mixture was stirred at room temperature overnight. The reaction mixture was then poured in ethyl acetate-water and the insolubles were filtered off. After phase separation, the aqueous layer was extracted with chloroform. The organic layers were combined and concentrated to dryness under reduced pressure, and the residue was subjected to column chromatography (silica gel; chloroform-methanol) and washed with ether-isopropyl ether to provide 0.14 g of N-(5-methyl-4,5,6,7-tetrahydrothiazolo[5,4-c]pyridin-2-yl)-o-methoxybenzamide melting at 164°–166° C.

Physicochemical properties:

| Elemental analysis (for C$_{15}$H$_{17}$N$_3$O$_2$S.0.4H$_2$O): | | | | |
|---|---|---|---|---|
| | C(%) | H(%) | N(%) | S(%) |
| Calcd. | 58.01 | 5.78 | 13.53 | 10.32 |
| Found | 58.05 | 5.51 | 13.37 | 10.35 |

Mass spectrum (EI): m/z 303 (M$^+$)

Example 4

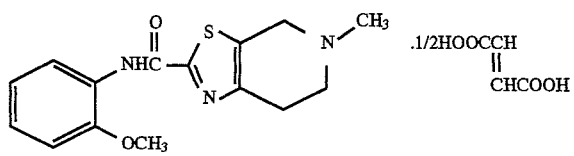

(1) To 8 ml of water were added 1.02 g of the compound obtained in Example 2-(1), 1.14 g of cuprous bromide and 5.1 ml of 48% aqueous hydrogen bromide solution. To this solution, 0.62 g of sodium nitrite was added in small portions at −5° C. The temperature was increased to 20° C. over a period of 30 minutes, and the reaction mixture was neutralized with sodium hydrogencarbonate and extracted with chloroform. The extract was concentrated to dryness under reduced pressure and purified by column chromatography (silica gel; chloroform-methanol) to provide 0.96 g of 2-bromo-5-methyl-4,5,6,7-tetrahydrothiazolo[5,4-c]pyridine.

Physicochemical properties:

$^1$H Nuclear magnetic resonance spectrum (δ, CDCl$_3$): 2.50 (s, 3H), 2.8–3.0 (m, 4H), 3.55–3.75 (m, 2H )

Mass spectrum (EI): m/z 232, 234 (M$^+$)

(2) In an argon stream, 4.5 ml of 15% n-butyllithium-hexane was added to 80 ml of dry ether at −60° C. At −70° C. solution of 0.95 g of the compound obtained in (1) in 15 ml of dry ether was added dropwise over a period of 1 hour. This solution was dropped onto dry ice in dry ether and, 30 minutes later, hydrogen chloride-ethyl acetate was added. The resulting solution was concentrated to dryness under reduced pressure and a portion thereof (0.59 g) was added to 5 ml of DMF. Then, 0.25 g of triethylamine, 0.24 g of HOBT and 0.37 g of DCC were serially added. Finally, 0.22 g of anisidine was added and the mixture was stirred at room temperature overnight.

The reaction mixture was poured in water and extracted with chloroform. The organic layer was concentrated to dryness under reduced pressure. The residue was purified by column chromatography (silica gel; chloroform-methanol) and treated with a suitable amount of fumaric acid in methanol to provide 0.17 g of N-(o-methoxyphenyl)-5-methyl-4,5,6,7-tetrahydrothiazolo[5,4-c]pyridine-2-carboxamide hemifumarate.

Physicochemical properties:

Melting point: 196°–198° C.

| Elemental analysis (for C$_{15}$H$_{17}$N$_3$O$_2$S.1/2C$_4$H$_4$O$_4$): | | | |
|---|---|---|---|
| | C(%) | H(%) | N(%) | S(%) |
| Calcd. | 56.50 | 5.30 | 11.63 | 8.87 |
| Found | 57.04 | 5.72 | 11.56 | 8.51 |

Mass spectrum (EI): m/z 303 (M$^+$, free compound)

Example 5

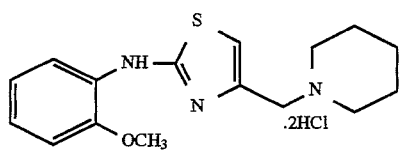

In 40 ml of acetone, 4.0 g of 1-(o-methoxyphenyl)-thiourea and 3.0 g of dichloroacetone were stirred together at room temperature for 2 days. The resulting crystals were recovered by filtration and dissolved in 60 ml of ethanol containing 9.3 g of piperidine. Then, the solution was stirred at room temperature for 20 hours.

The solvent was distilled off under reduced pressure, and the residue was diluted with water, made basic with potassium carbonate and extracted with ether. The ether layer was dried over anhydrous magnesium sulfate and concentrated under reduced pressure, and the residue was treated with hydrochloric acid and recrystallized from ethanol to provide 6.3 g of 2-(o-methoxyanilino)-4-piperidinomethylthiazole dihydrochloride.

Physicochemical properties:

Melting point: 166°–169° C.

| Elemental analysis (for C$_{16}$H$_{23}$N$_3$OSCl$_2$): | | | | | |
|---|---|---|---|---|---|
| | C(%) | H(%) | N(%) | O(%) | S(%) | Cl(%) |
| Calcd. | 51.06 | 6.16 | 11.17 | 4.25 | 8.52 | 18.84 |
| Found | 51.08 | 6.20 | 11.12 | | 8.48 | 18.80 |

Example 6

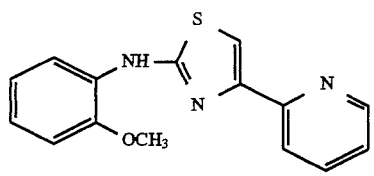

In 20 ml of ethanol, 0.5 g of 1-(o-ortho-methoxy-phenyl) thiourea and 0.77 g of 2-bromoacetylpyridine hydrobromide were refluxed together for 1 hour. The solvent was then distilled off under reduced pressure, and the residue was diluted with water, made basic with potassium carbonate and extracted with ethyl acetate.

The ethyl acetate layer was dried over anhydrous magnesium sulfate and concentrated under reduced pressure, and the residue was recrystallized from ethanol to provide 0.71 g of 2-(o-methoxyanilino)-4-(2-pyridyl)thiazole.

Physicochemical properties:

Melting point: 165°–166° C.

| Elemental analysis (for C$_{15}$H$_{13}$N$_3$OS): | | | |
|---|---|---|---|
| | C(%) | H(%) | N(%) | S(%) |
| Calcd. | 63.58 | 4.62 | 14.83 | 11.32 |
| Found | 63.66 | 4.60 | 14.90 | 11.26 |

We claim:

1. A thiazole derivative of formula (I):

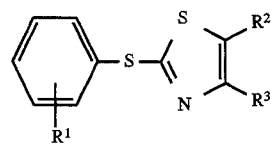

wherein R$^1$ is a lower alkoxy group,

R$^2$ and R$^3$ are either such that (i) R$^2$ is a hydrogen atom and

R$^3$ is —Y—Het wherein Y is a single bond or a lower alkylene group and Het is selected from the group consisting of pyrrolidinyl, pyrrolyl, piperidyl or 2-pyridyl or (ii) $R^2$ and $R^3$ combined together is a group of the formula

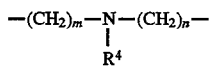

where m and n each is 1 or 2 and $R^4$ is a lower alkyl group), and X is selected from the group consisting of

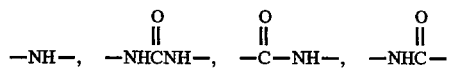

or a pharmaceutically acceptable salt thereof.

2. A pharmaceutical composition comprising a pharmacologically effective amount of the thiazole derivative (I) or a pharmaceutically acceptable salt thereof as claimed in claim 1 and a pharmaceutically acceptable carrier.

3. A method for treating senile constipation, atonic constipation, diabetic motor disorder of the digestive tract, postoperative motor disorder of the digestive tract, retention of gastric contents, dyspepsia, flatulence, schizophrenia, depression, anxiety and/or dysmnesia which comprises administering a therapeutically effective amount of the compound as claimed in claim 1 or a pharmaceutically acceptable salt thereof.

4. A method for producing a thiazole derivative of the general formula (I):

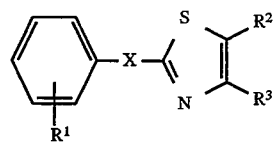

(wherein $R^1$ means a hydrogen atom or a lower alkoxy group, $R^2$ and $R^3$ are either such that $R^2$ means a hydrogen atom and $R^3$ means a group of the formula —Y—Het (where Y means a single bond or a lower alkylene group and Het means a nitrogen-containing heterocyclic group) or such that $R^2$ and $R^3$ combined together mean a group of the formula

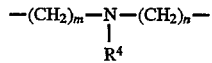

(where m and n each means 1 or 2 and $R^4$ means a lower alkyl group), and X means a group represented by one of the formulas: —NH—,

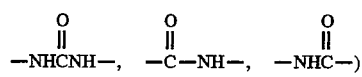

or a pharmaceutically acceptable salt thereof, comprising (a) reacting a thiourea derivative of the general formula (II):

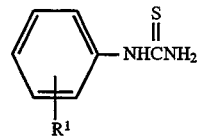

(wherein $R^1$ has the meaning defined above) with an α-halogenoketone derivative of the general formula (III):

(wherein $R^2$ and $R^3$ have the meanings respectively defined above, and Z means a halogen atom) to give a thiazole derivative of the general formula (Ia):

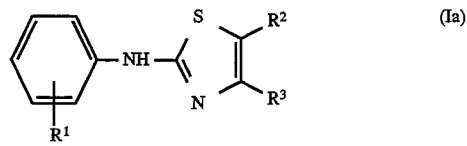

(wherein $R^1$, $R^2$ and $R^3$ have the meanings respectively defined above ); or (b) reacting an isocyanate derivative of the general formula (IV):

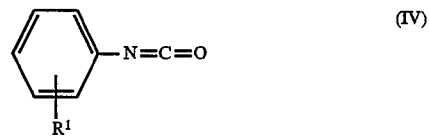

(wherein $R^1$ has the meaning defined above) with an amine derivative of the general formula (V):

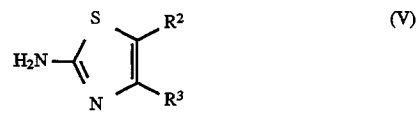

(wherein $R^2$ and $R^3$ have the meanings respectively defined above) to give an urea derivative of the general formula (Ib):

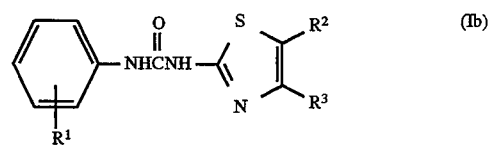

(wherein $R^1$, $R^2$ and $R^3$ have the meanings respectively defined above); or (c) reacting a carboxylic acid derivative of the general formula (VI):

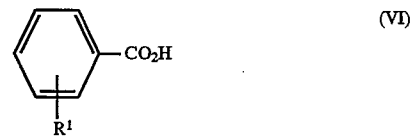

(wherein $R^1$ has the meaning defined above) with an amine derivative of the general formula (V):

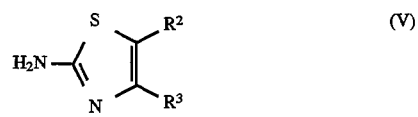

(wherein $R^2$ and $R^3$ have the meanings respectively defined above) to give an amide derivative of the general formula (Ic):

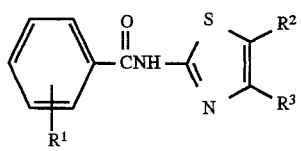

(wherein $R^1$, $R^2$ and $R^3$ have the meanings respectively defined above); or (d) reacting an amine derivative of the general formula (VII):

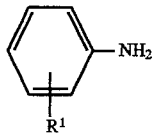

(wherein $R^1$ has the meaning defined above) with a carboxylic acid derivative of the general formula (VIII):

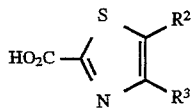

(wherein $R^2$ and $R^3$ have the meanings respectively defined above) to give an amide derivative of the general formula (Id):

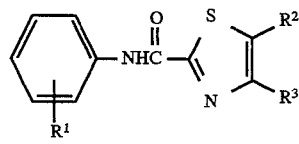

(wherein $R^1$, $R^2$ and $R^3$ have the meanings respectively defined above).

5. A method for treating schizophrenia or depression which comprises administering a therapeutically effective amount of a thiazole derivative of formula (I):

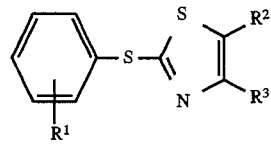

wherein $R^1$ is a lower alkoxy group, $R^2$ and $R^3$ are either such that (i) $R^2$ is a hydrogen atom and $R^3$ is —Y—Het wherein Y is a single bond or a lower alkylene group and Het is a nitrogen-containing heterocyclic group or (ii) $R^2$ and $R^3$ combined together is a group of the formula formula

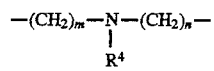

where m and n each is 1 or 2 and $R^4$ is a lower alkyl group), and X is selected from the group consisting of:

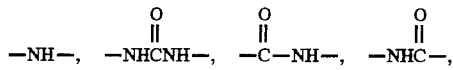

or a pharmaceutically acceptable salt thereof.

6. A derivative according to claim 1, wherein Het is pyrrolidinyl.

7. A derivative according to claim 1, wherein Het is pyrrolyl.

8. A derivative according to claim 1, wherein Het is piperidyl.

9. A derivative according to claim 1, wherein Het is 2-pyridyl.

* * * * *